United States Patent [19]

Kendall et al.

[11] Patent Number: 4,623,431

[45] Date of Patent: Nov. 18, 1986

[54] POLYMERIZATION INHIBITOR FOR VINYL AROMATIC COMPOUNDS

[75] Inventors: Debra L. Kendall, Hornick, Iowa; James R. Butler; Kevin P. Menard, both of Big Spring, Tex.

[73] Assignee: Cosden Technology, Inc., Dallas, Tex.

[21] Appl. No.: 756,155

[22] Filed: Jul. 18, 1985

[51] Int. Cl.$^4$ ............................................. B01D 3/34
[52] U.S. Cl. .......................................... 203/9; 203/49; 203/68; 203/91; 585/5
[58] Field of Search ............... 203/8, 9, 49, 68, 69, 203/70, 91; 585/5

[56] References Cited

U.S. PATENT DOCUMENTS

| | | | |
|---|---|---|---|
| 2,188,772 | 1/1940 | Driesbach et al. | 203/9 |
| 2,677,617 | 5/1954 | Thompson | 585/5 |
| 3,527,822 | 9/1970 | Benson, Jr. | 203/9 |
| 3,531,540 | 9/1970 | Marshall et al. | 203/9 |
| 3,647,637 | 3/1972 | Rosenwald | 203/9 |
| 3,838,019 | 9/1974 | Schwerdtel | 203/49 |
| 4,177,110 | 12/1979 | Watson | 203/9 |
| 4,265,711 | 5/1981 | Gleim | 203/9 |
| 4,371,428 | 2/1983 | Montagna | 585/808 |

OTHER PUBLICATIONS

Hack's Chemical Dictionary, 4th ed., McGraw Hill Book Co., p. 65, 1972.

*Primary Examiner*—S. Leon Bashore
*Assistant Examiner*—Virginia Manoharan
*Attorney, Agent, or Firm*—John K. Abokhair; M. Norwood Cheairs

[57] ABSTRACT

A process for the distillation of readily polymerizable vinyl aromatic compounds which comprises subjecting said compounds to distillation conditions in the presence of oxygen and an effective amount of asphaltene as a polymerization inhibitor.

18 Claims, No Drawings

POLYMERIZATION INHIBITOR FOR VINYL AROMATIC COMPOUNDS

FIELD OF THE INVENTION

The present invention relates to a process for the distillation of readily polymerizable vinyl aromatic compounds, and more especially, to a process for the vacuum distillation of styrene, substituted styrene, divinylbenzene and polyvinylbenzenes wherein the amount of said materials polymerized during distillation is reduced over an extended period of time, wherein the rate of throughput for a given distillation apparatus can be increased over the rate at which such apparatus may be operated in accordance with conventional methods.

BACKGROUND OF THE INVENTION

It is well known that vinyl aromatic compounds such as monomeric styrene, lower alkylated styrene, e.g., alphamethyl styrene, and divinylbenzene polymerize readily, and furthermore, that the rate of polymerization increases with increasing temperature. Inasmuch as styrene and divinylbenzene produced by common industrial methods contain impurities, these compounds must be subjected to separation and purification processes in order to be suitable for most types of further industrial use. Such separation and purification is generally accomplished by distillation.

In order to prevent polymerization during distillation of vinyl aromatic compounds, various types of known polymerization inhibitors have been employed in connection with prior art distillation processes. For example, common inhibitors useful for inhibiting the polymerization of vinyl aromatics under distillation conditions include nitrated phenols.

In a typical distillation process for vinyl aromatic compounds utilizing a polymerization inhibitor, the mixture of vinyl aromatic to be distilled is generally contacted with the chemical polymerization inhibitor prior to being subjected to distillation conditions in the distillation apparatus. It remains as a significant problem today that the amount of polymer formed in the distillation apparatus and in the high purity product recovered therefrom is substantially higher than desired, and occasionally, that complete polymerization occurs inside of the distillation apparatus.

Although many compounds are effective for inhibiting the polymerization of vinyl aromatic compounds under differing conditions, e.g., storage, other purification techniques, etc., for a number of reasons which are not entirely understood in view of the diverse and unpredictable results obtained, only extremely few of these compounds have proved to be of any utility for inhibiting vinyl aromatic polymerization under distillation conditions, particularly under vacuum distillation conditions. In addition, certain compounds which are useful for inhibiting polymerization of one type of vinyl aromatic compound, for example, styrene, have proved to be essentially ineffective for inhibiting polymerization of another species of vinyl aromatic compound, for example, divinylbenzene. A limited number of nitroso compounds have proven to be effective for inhibiting polymerization of styrene monomer during distillation. For example, N-nitroso phenylhydroxylamine and p-nitroso-N,N-dimethylaniline are reasonably effective inhibitors for the distillation of styrene, although they are not particularly soluble in styrene monomer. On the other hand, N-nitroso diphenylamine disclosed in U.S. Pat. No. 3,816,265, assigned to the assignee of the present application has been demonstrated to be a particularly effective polymerization inhibitor under vacuum distillation conditions for both styrene and divinylbenzene, whereas N,N-nitrosomethylamine has been found to be an excellent polymerization inhibitor for styrene under vacuum distillation conditions. One of the most effective inhibitor systems known for divinylbenzene comprises a mixture of sulfur and N-nitroso phenylhydro- xylamine.

U.S. Pat. No. 3,786,110 teaches that in a process for the pyrolysis of hydrocarbons or substituted hydrocarbons in a high temperature zone (about 1200° C.) followed by rapid cooling in a quench zone, the serious problem of formation of hard deposits on the interior of apparatus downstream from the quench zone is solved by adding asphaltenes to the pyrolysis product in or just after the quench zone. The asphaltenes provide sites for polymer molecules to attach themselves; also asphaltenes are capable of reacting with the highly reactive polyolefins to form low molecular weight polymers, thus preventing the formation of high molecular weight products. In contrast, in the process of the present invention and the applicable commercial applications, the formation of even low molecular weight polymers is not acceptable.

U.S. Pat. No. 4,376,678 to Partos teaches the utilization of 2,2-bis(3,5-dinitro-4-hydroxyphenyl) propane as a polymerization inhibitor. The Partos patent contains a listing and discussion of several U.S. and foreign patents and document which relate to polymerization inhibitors. Each of the patents or articles relates to a specific chemical compound utilized as a polymerization inhibitor.

As can be seen from the above, a readily available and less costly polymerization inhibitor would be desirable.

SUMMARY OF THE INVENTION

It is therefore an object of the present invention to provide both a polymer inhibiting composition and a process for inhibiting the polymerization of vinyl aromatic compounds.

Another object of the invention is to provide both a polymer inhibiting composition and a process for inhibiting the polymerization of vinyl aromatic compounds at higher temperatures resulting in a higher recovery of high purity, unsaturated vinyl aromatic compounds while decreasing the production of undesirable by-products.

A still further object of the invention resides in the provision of both a polymer inhibiting composition and a process for inhibiting the polymerization of vinyl aromatic compounds which permits the distillation apparatus to be operated at a higher temperature and an increased rate of throughput without a reduction in efficiency.

In accomplishing the foregoing and other objects, there has been provided in accordance with the present invention a process for inhibiting polymerization during the distillation of readily polymerizable vinyl aromatic compounds by carrying out the distillation in the presence of oxygen and an effective amount of asphaltenes.

The vinyl aromatic compounds covered in the present invention include styrene, substituted styrene, divinylbenzene, vinyltoluene, vinyl naphthalene and the polyvinylbenzenes. This group is also understood to include all structural isomers thereof.

According to the present process, the amount of polymerization occurring within the distillation apparatus at temperatures as high as 150° C. is significantly reduced in comparison with conventionally employed methods. In addition, the distillation apparatus may be operated at a higher temperature and pressure than when using conventional inhibitors thereby allowing a higher rate of distillation throughput.

Further objects, features, and advantages of the invention will become apparent from the detailed description which follows and from the claims.

DETAILED DESCRIPTION OF THE PREFERRED EMBODIMENTS

The distillation process of the present invention employs asphaltenes as a polymerization inhibitor during the distillation of vinyl aromatic compounds, especially styrene, for the purification thereof. The distillation process may be conducted over wide-ranging parameters including reduced pressure distillation (i.e., vacuum distillation) and atmospheric distillation (i.e., open to the atmosphere) and over a fairly broad range of temperatures, from about 65° to about 150° C. One of the most significant advantages of the invention, in addition to the broad operative ranges of pressure and temperature and the reduction of unwanted polymerization, is that readily available asphaltenes are utilized as the inhibitor. Asphaltenes are probably the least expensive cut of petroleum.

Asphalts, or asphaltenes, are the bottom products resulting from crude oil distillation. The asphaltene fraction represents the largest most polar compound types in crude oil. At higher molecular weight, i.e., greater than 800, the probability of a polar function is very high and little or no pure hydrocarbon types exist. A chromographic separation of (n-pentane) asphaltenes from Wilmington residium produced only 5% hydrocarbon material. Heptane precipitation would produce asphaltenes containing even less hydrocarbon. The polar material isolated in this separation consisted primarily of acids which suggests that acid-base interactions are not important in asphaltene precipitation. Principal polar functionalities identified include carboxylic acids, phenols, amides, carbazoles, and pyridine benzologs. Typically, asphaltenes contain 40-50% aromatic carbon and have molecular weights of several thousand. While the specific composition of asphaltenes is not clearly defined, asphaltenes are well known in the art and are easily identified by those skilled in the art.

The distillation technique of the process of the present invention is suitable for use in virtually any type of distillative separation of a readily polymerizable vinyl aromatic compound from a mixture wherein the vinyl aromatic compound is subjected to temperatures above room temperature. Surprisingly, the process of the present invention has been found adaptable to reduced pressure distillation techniques (vacuum distillation) as well as atmospheric distillation techniques. Air or oxygen must be added to the system in order that the inhibitor exhibits efficacy.

The oxygen employed in combination with the asphaltenes in accordance with the present invention may be in the form of oxygen or an oxygen-containing gas. Of course, if an oxygen-containing gas is employed, the remaining constituents of the gas must be inert to the vinyl aromatic compounds under the distillation conditions. The most useful, practical and least expensive source of oxygen is, of course, air which is preferred for the present invention. The amount of oxygen employed may vary widely but generally will be approximately that found in air.

The amount of polymerization inhibitor added may vary over a wide range depending upon the conditions of distillation. Generally, the degree of stabilization is proportional to the amount of inhibitor added. In accordance with the present invention, it has been found that inhibitor concentrations between about 0.01 and 5.0 weight percent asphaltenes in combination with air or oxygen have generally provided suitable results, depending primarily upon the temperature of the distillation mixture and the degree of inhibition desired.

During distillation of the vinyl aromatic mixtures, the temperature of the reboiler is preferably maintained from about 65° to about 150° C. Preferred, however, is a temperature range within the range of from about 90° to about 143° C. Under such conditions, in a distillation apparatus having a distillation zone containing from about 50 to 100 distillation stages, inhibitor concentrations of from about 0.01 to about 5.0 weight percent (wt. %) asphaltenes are suitable, whereas concentrations of from about 0.1 to about 3 wt. % asphaltenes in combination with air or oxygen are preferred. Obviously, amounts of inhibitor greater than those specified hereinabove may be employed, although the advantages of adding the additional inhibitor are not significant and are outweighed by the corresponding increase in the cost and difficulty of handling.

The polymerization inhibitor of the present invention may be introduced into the distillation apparatus in any convenient manner which permits efficient distribution of the inhibitor throughout the apparatus. The inhibitor may be added to the incoming stream of styrenic material, into the reboiler area of the distillation column, or at any other convenient location. It is preferred to add the inhibitor composition at the top of the distillation column. Since the inhibitor is heavier than the distilled monomer, the inhibitor would flow downwards through the distillation column. This assures the presence of inhibitor throughout the distillation column as well as in the distillation flask.

Since the inhibitor is gradually depleted during operation, it is generally necessary to maintain the appropriate amount of inhibitor in the distillation apparatus by adding inhibitor during the course of the distillation process. Such addition may be carried out either on a generally continuous basis or it may consist of intermittent charging of inhibitor into the distillation system. The means by which the maintenance of the necessary inhibitor concentration is carried out is of no particular importance provided the concentration of inhibitor is maintained above the minimum required level.

Use of the polymerization inhibitor system of the present invention enables the distillation apparatus to operate at an increased rate as opposed to conventional prior art processes since the inhibitor of the present invention is more efficient and will thus permit higher distillation temperatures at higher pressures. In this manner, the rate of distillation may be increased without increasing the amount of polymerization which has been deemed to be acceptable in accordance with conventional distillation procedures. Most significantly, the use of inexpensive asphaltenes, does not add significant amounts to the cost of production or distillation of the desired vinyl aromatic compounds.

Upon recovery of the distillation product obtained from the process of the present invention, it is found that a higher percentage of the pure readily polymerizable vinyl aromatic compound is recovered in an unpolymerized state, and that the inhibitor employed does not derogate from the ability of the recovered monomer to undergo subsequent polymerization.

In order to more fully describe the present invention, the following examples are presented which are intended to be merely illustrative and not in any sense definitive of the limits of the invention.

For comparative purposes, it should be noted that without an inhibitor, styrene at approximately 118° C. polymerizes in about 0.5 hours.

In the first set of experiments, 50 grams of styrene monomer were placed in a 100 ml. reaction flask fitted with a magnetic stirrer and heated in a stirred oil bath to about 118° C.+1° C. The reaction flask was also fitted with proper closures for the addition of inhibitor and gases to control the distillation atmosphere, i.e., air purge or nitrogen atmosphere. Samples were removed periodically from the reaction flask and tested for polymer content. The results are shown in Table I below.

TABLE I

| Inhibitor | Minutes to reach 10% Polymer Content | Minutes to reach 30% Polymer Content |
|---|---|---|
| 1. 1% asphaltenes under $N_2$ | 115 | 215 |
| 2. 200 ppm DNPC | 140 | 305 |
| 3. 0.1% asphaltenes in air | 195 | 260 |
| 4. 0.1% of 226° C. m.p. Asphalt in air | 185 | 260 |
| 5. 1% asphaltenes in air | not reached after 350 min. | — |
| 6. 1% of 206° C. m.p. asphalt in air | not reached after 350 min. | — |
| 7. 1% asphaltenes under $N_2$ with 100 ppm BPO | (immediately had 20% polymer) | 15 min. |
| 8. 1% asphaltenes under $N_2$ with 20 ppm TBP | 65 | 340 |

As can be seen from the above, when 1% by weight asphaltenes under nitrogen atmosphere were added to styrene monomer, it took 215 minutes to reach 30% by weight (wt. %) polymer content as compared to complete polymerization in 30 minutes without the asphaltenes. However, the addition of air, i.e., oxygen, led to substantially improved results. In the presence of air and 1 wt. % asphalt or asphaltenes, 10 wt. % polymer content was not reached even after 350 minutes of distillation. This translates to at least a 300% improvement over the same conditions in the absence of air or oxygen. Furthermore, 0.1 wt. % asphalts or asphaltenes in air were significantly more effective than 1 wt. % (ten times the amount) under nitrogen atmosphere.

Styrene containing 1 wt. % asphaltenes was heated to 118° C. (224° F.) while air was gently bubbled through the solution. In five (5) hours, less than 5% polymerization was observed in contrast to the almost 50% obtained under an inert atmosphere, i.e., $N_2$. A control run with 200 ppm DNPC, 20% polymerization occurred under the same conditions.

What is claimed is:

1. A proess for the distillation of polymerizable vinyl aromatic compounds which comprises subjecting said compounds to distillation conditions in the presence of oxygen and an effective amount of asphaltene to substantially inhibit polymerization.

2. The process of claim 1 wherein the vinyl aromatic compound is selected from the group consisting of styrene, substituted styrene, divinylbenzene, vinyltoluene, vinyl naphthalene, polyvinylbenzenes and structural isomers thereof.

3. The process of claim 1 wherein the asphaltene concentration is from about 0.01 to about 5.0 percent by weight.

4. The process of claim 1 wherein the asphaltene concentration is from about 0.1 to 3.0 percent by weight.

5. The process of claim 1 wherein the distillation is carried out at a temperature of from about 65° to about 150° C.

6. The process of claim 1 wherein the distillation is carried out at a temperature of from about 90° to about 143° C.

7. The process of claim 1 wherein the oxygen is present as air.

8. A process for the distillation of polymerizable vinyl aromatic compounds which comprises subjecting said compounds to distillation temperatures of from about 65° C. to about 150° C. in the presence of oxygen and from about 0.01 to about 5.0 percent by weight asphaltenes.

9. The process of claim 8 wherein the asphaltene concentration is from about 0.1 to 3.0 percent by weight.

10. The process of claim 8 wherein the distillation is carried out at a temperature of from about 90° to about 143° C.

11. The process of claim 8 wherein the oxygen is present as air.

12. The process of claim 8 wherein the vinyl aromatic compound is selected from the group consisting of styrene, substituted styrene, divinylbenzene, vinyltoluene, vinyl naphthalene, polyvinylbenzenes and structural isomers thereof.

13. A process for the distillation of polymerizable vinyl aromatic monomers which comprises:
   (a) introducing said vinyl aromatic monomers into a distillation flask with from about 0.01 to about 5.0 weight percent asphaltenes,
   (b) subjecting the mixture to distillation conditions while bubbling oxygen through the mixture, and
   (c) recovering said vinyl aromatic monomer.

14. The process of claim 13 wherein the vinyl aromatic compound is selected from the group consisting of styrene, substituted styrene, divinylbenzene, vinyltoluene, vinyl naphthalene, polyvinylbenzenes and structural isomers thereof.

15. The process of claim 13 wherein the asphaltene concentration is from about 0.1 to 3.0 percent by weight.

16. The process of claim 13 wherein the distillation is carried out at a temperature of from about 65° to about 150° C.

17. The process of claim 13 wherein the distillation is carried out at a temperature of from about 90° to about 143° C.

18. The process of claim 13 wherein the oxygen is present as air.

* * * * *